United States Patent [19]

Yazawa et al.

[11] Patent Number: 5,455,644
[45] Date of Patent: Oct. 3, 1995

[54] OPHTHALMOLOGIC APPARATUS HAVING AN EXAMINING SYSTEM FOR EXAMINING THE FUNDUS OF AN EYE

[75] Inventors: Koji Yazawa, Tachikawa; Kazunobu Kobayashi, Yokohama; Kazuhiro Matsumoto, Kawasaki; Shinya Tanaka, Tokyo, all of Japan

[73] Assignee: Canon Kabushiki Kaisha, Tokyo, Japan

[21] Appl. No.: 23,114

[22] Filed: Feb. 26, 1993

[30] Foreign Application Priority Data

Feb. 28, 1992 [JP] Japan .................................. 4-078891
May 22, 1992 [JP] Japan .................................. 4-155829

[51] Int. Cl.⁶ .................................................. A61B 3/14
[52] U.S. Cl. ........................ 351/206; 351/211; 351/221; 354/62
[58] Field of Search ..................... 351/206, 208, 351/211, 215, 216, 221; 354/62

[56] References Cited

U.S. PATENT DOCUMENTS

| | | | |
|---|---|---|---|
| 4,690,525 | 9/1987 | Kobayashi et al. | 351/206 |
| 4,820,037 | 4/1989 | Kohayakawa et al. | 351/211 |
| 4,848,896 | 7/1989 | Matsumoto | 351/211 |
| 4,900,145 | 2/1990 | Akiyama | 351/221 |
| 4,952,049 | 8/1990 | Matsumoto | 351/211 |
| 4,988,184 | 1/1991 | Akiyama | 351/221 |
| 4,991,584 | 2/1991 | Kobayashi et al. | 351/211 |
| 5,233,372 | 8/1993 | Matsumoto | 351/206 |
| 5,300,964 | 4/1994 | Kobayashi | 354/62 |

FOREIGN PATENT DOCUMENTS

2-302243  12/1990  Japan .

Primary Examiner—Richard A. Bertsch
Assistant Examiner—Howard R. Richman
Attorney, Agent, or Firm—Fitzpatrick, Cella, Harper & Scinto

[57] ABSTRACT

An ophthalmologic apparatus has an illuminating system for illuminating the fundus of an eye to be examined with infrared light from substantially the front of the eye to be examined through a pupil area, the illuminating system having a light source, and an image pickup camera for receiving infrared reflected light from the fundus of the eye to be examined illuminated by the illuminating system on an image pickup surface conjugate with the front eye part of the eye to be examined. The turbid state of the light transmitting body portion of the eye to be examined can be ascertained by the image output from the image pickup camera.

27 Claims, 6 Drawing Sheets

OPHTHALMOLOGIC APPARATUS HAVING AN EXAMINING SYSTEM FOR EXAMINING THE FUNDUS OF AN EYE

BACKGROUND OF THE INVENTION

1. Field of the Invention

This invention relates to an infrared ray observation ophthalmologic apparatus for use in ophthalmologic hospitals or the like.

2. Related Background Art

In recent years, apparatuses of the non-mydriasis type in which any mydriatic is not dripped onto an eye to be examined have entered the mainstream of ophthalmoscopic apparatuses, such as retinal cameras and refractometers. Generally, an ophthalmoscopic apparatus of the non-mydriasis type utilizes infrared light to illuminate the front eye part or fundus of an eye to be examined in order to prevent the contraction of the pupil of the eye, and carry out various types of examinations.

In the above-described example of the prior art, however, even when there is turbidity in the light transmitting body of the eye to be examined and a large error occurs in the measured refraction value or flare occurs in the image of the fundus of the eye to thereby cause the quality of the image to deteriorate, there is no means for positively ascertaining the causes thereof. Also, there are known cataract cameras for photographing cataracts which cause turbidity in the crystalline lens, and crystalline lens photographing cameras, but these are directed to entirely different uses and are not versatile.

SUMMARY OF THE INVENTION

It is a first object of the present invention to solve the above-noted problems and to provide an infrared ray observation ophthalmologic apparatus which can ascertain the turbidity of the light transmitting body of an eye to be examined which may become the cause of a flare in the image of the fundus or an abnormality in the measured value of the refractive power of the eye when the photographing of the fundus of the eye or the measurement of refraction is effected.

It is a second object of the present invention to provide a retinal camera which can effect thorough illumination observation of the crystalline lens of an eye to be examined which is free of direct reflection from a light source, to thereby determine, for example, the degree of turbidity of the eye.

It is a third object of the present invention to provide a retinal camera which can record the image of the fundus of the eye and the degree of turbidity thereof, as well as information of any ophthalmic trouble.

DETAILED DESCRIPTION OF THE PREFERRED EMBODIMENTS

An infrared ray observation ophthalmologic apparatus according to each of embodiments which will hereinafter be described is an ophthalmologic apparatus for observing the outer eye part of an eye to be examined by means of an infrared TV camera, characterized by the provision of means for projecting infrared light from the substantially front direction of the eye to be examined into the eye via the pupil area thereof to thereby illuminate the fundus of the eye, and ascertaining the turbid state of the light transmitting body portion of the eye from the shielded state of the eye fundus reflected light by the turbidity of the light transmitting body portion, by the output of the infrared TV camera.

The infrared ray observation ophthalmologic apparatus having the above-described construction projects infrared light into the eye to be examined, and observes the eye fundus reflected light intercepted by the turbidity of the light transmitting body of the eye to be examined.

The invention will hereinafter be described in detail with respect to some embodiments thereof.

Figure 1:
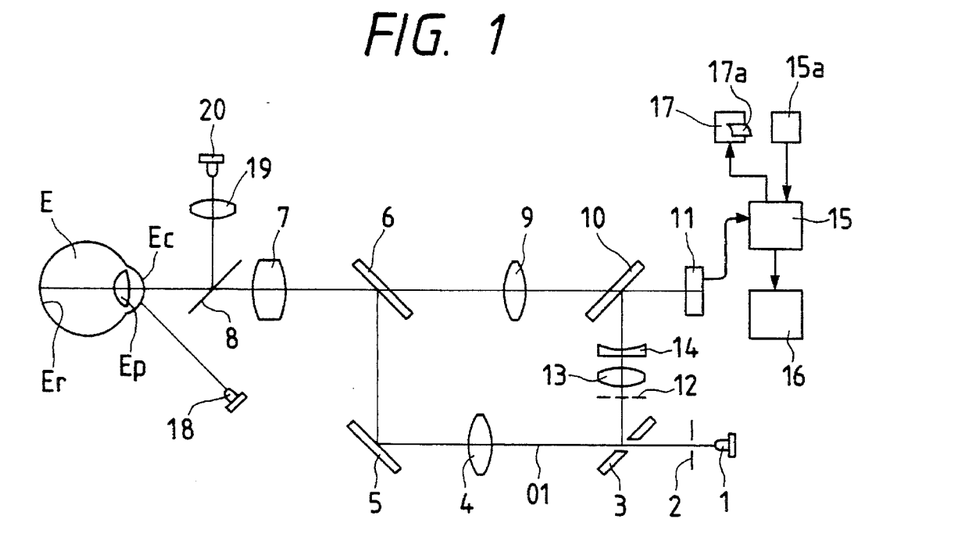
FIG. 1 shows the construction of a first embodiment of the present invention.
Figure 2:
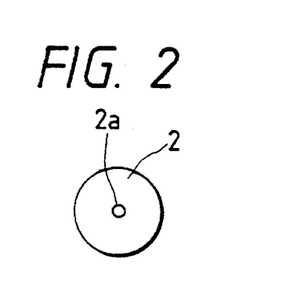
FIG. 2 is a plan view of a stop.
Figure 3:
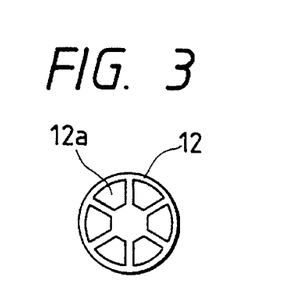
FIG. 3 is a plan view of a multiaperture mask.

FIG. 1 shows the construction of a first embodiment having a front eye part photographing function and an eye refraction measuring function. On the optical path 01 from an infrared light source 1 for refraction measurement emitting a light beam of a first wavelength to an eye E to be examined, there are provided in succession an aperture mask 2 having a central opening 2a as shown in FIG. 2, an apertured mirror 3, a projection lens 4, a mirror 5, a dichroic mirror 6 reflecting only the light beam of the first wavelength, an objective lens 7 and a dichroic mirror 8 transmitting the light beam of the first wavelength therethrough. Rearwardly of the dichroic mirror 6, there are provided in succession an imaging lens 9, a dichroic mirror 10 reflecting only the light beam of the first wavelength, and a TV camera 11 having a large detection wavelength width. Between the apertured mirror 3 and the dichroic mirror 10, there are disposed an aperture mask 12 having six apertures 12a as shown in FIG. 3, an imaging lens 13, and a multiprism 14 comprising six wedge-shaped prisms. The output of the TV camera 11 may be analyzed by a signal processor 15 and output by a TV monitor 16 or a printer 17.

A front eye part illuminating infrared light source 18 emitting a light beam of a second wavelength is disposed in front of and below the eye E to be examined, and a projection lens 19 and an eye interior illuminating infrared light source 20 emitting a light beam of a third wavelength are provided in the incidence direction of the dichroic mirror 8. The dichroic mirror 8 has the characteristic of reflecting a part of the light beam of the third wavelength and transmitting a part of this light beam therethrough, and the image of the eye interior may be picked up by the TV camera 11. The aperture mask 2 and the image pickup surface of the TV camera 11 are conjugate with the fundus Er of the eye E to be examined, and the aperture mask 12 is substantially conjugate with the cornea Ec of the eye to be examined and further, the image pickup surface of the TV camera 11 is in a conjugate relation with the front eye part for the wavelengths of the light sources 18 and 20 and is conjugate with the fundus of the eye for the wavelength of the light source 1.

Figure 4:
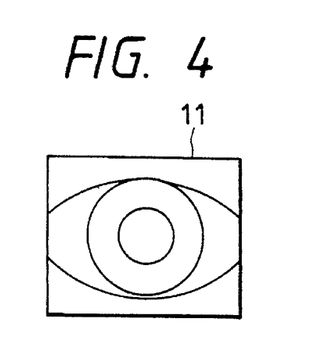
FIG. 4 illustrates the photographed image of the front eye part.
Figure 5:
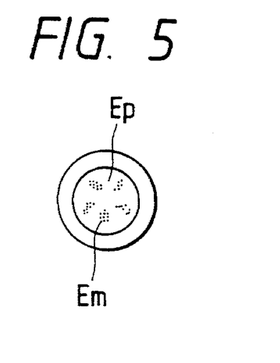
FIG. 5 is an illustration of an eye to be examined having a turbid portion.

The front eye part reflected light from the infrared light source 18 is transmitted through the dichroic mirror 8, the objective lens 7 and the dichroic mirror 6 in succession and is received by the TV camera 11 via the imaging lens 9 and the dichroic mirror 10, and the image of the front eye part is picked up by the TV camera 11, as shown in FIG. 4. In this state, the pupil Ep is dark, but when the eye interior illuminating infrared light source 20 is turned on to illuminate the interior of the eye, if there is a turbid portion in the eye E to be examined because of a cataract or the like, the turbid portion Em as shown in FIG. 5 will intercept the eye fundus reflected light and therefore, the pupil Ep will appear as a dark image on the TV monitor 16. The TV signal at this time is once stored in the signal processor 15. A switch 15a for reproducing the stored image of the front eye part on the monitor is connected to the signal processor, and the stored image can be reproduced and shown to the examinee.

Figure 6:
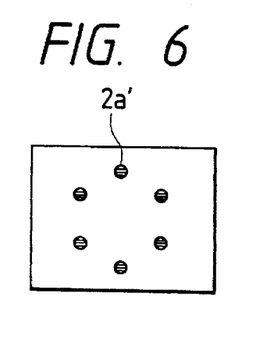
FIG. 6 shows an image photographed by a TV camera during the measurement of refraction.

When effecting refraction measurement, the refraction measuring infrared light source 1 emits light and the light beam passes through the optical path 01 to the eye E to be examined. The light reflected by the fundus Er of the eye E to be examined returns halfway by the same route, is reflected by the apertured mirror 3 and is picked up by the TV camera 11 via the aperture mask 12, the imaging lens 13, the multiprism 14 and the dichroic mirror 10. This picked-up image is made into the six images of the aperture mask 2 as shown in FIG. 6, and from the positional relation among the six images 2a', the value of eye refraction is found by the signal processor 15.

Figure 7:
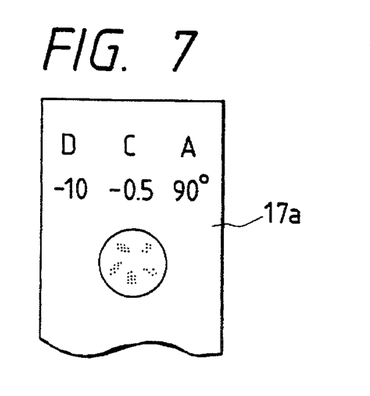
FIG. 7 illustrates recording paper.

After the measurement of the refraction value, the refraction value and the image stored in the signal processor 15 are printed on recording paper 17a by the printer 17, as shown in FIG. 7. Whether the refraction value is abnormal and whether it is due to the turbidity of the interior of the eye can be ascertained on the spot from the recording paper 17a. The dichroic mirror 8 may also be designed to be retractable out of the optical path except during the ascertainment of turbidity, and the front eye part illuminating infrared light source 18 may be utilized instead of the eye interior illuminating infrared light source 20.

Figure 8:
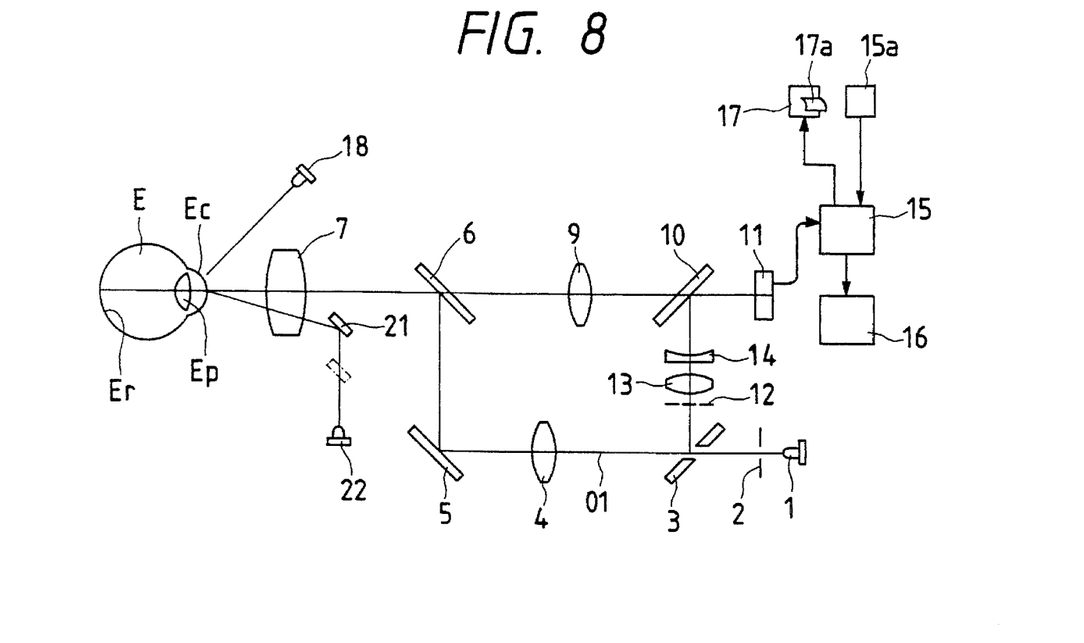
FIG. 8 shows the construction of a second embodiment of the present invention.

FIG. 8 shows the construction of a second embodiment which is a modification of the first embodiment. A vertically movable mirror 21 and an eye interior illuminating infrared light source 22 are provided rearwardly of the objective lens 7 so as not to overlap the optical path 01.

During the photographing of the front eye part, the front eye part illuminating infrared light source 18 and the eye interior illuminating infrared light source 22 are turned on to illuminate the front eye part and the interior of the eye through the intermediary of the mirror 21. The image of the front eye part is picked up by the TV camera 11, is stored in the signal processor 15, and is output with the value of eye refraction as in the first embodiment. Since the mirror 21 is located rearwardly of the objective lens 7, the operation distance between the ophthalmoscopic apparatus and the eye E to be examined can be made sufficiently large to thereby lessen the examinee's feeling of discomfort.

Figure 9:
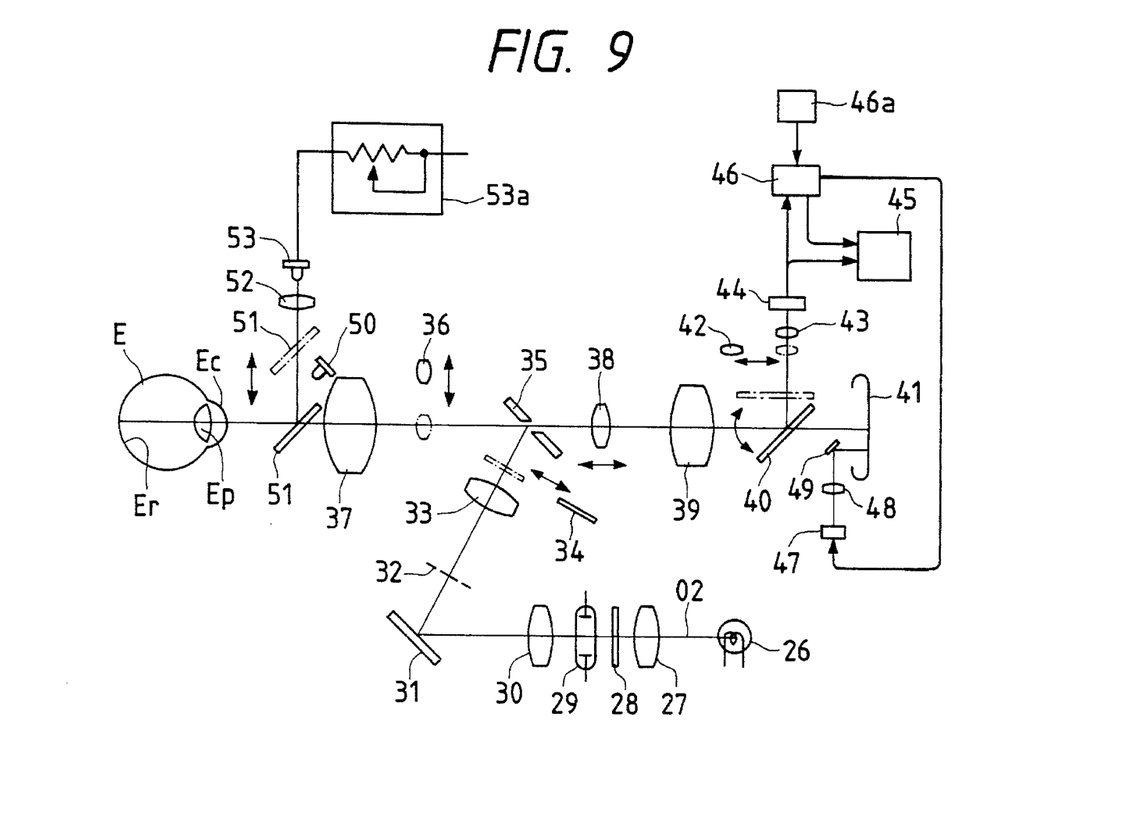
FIG. 9 shows the construction of a third embodiment of the present invention.

FIG. 9 shows the construction of a third embodiment. On the optical path 02 from a light source 26 to the eye E to be examined, there are disposed in succession a lens 27, an infrared filter 28, an eye fundus photographing light source 29 as a white light source such as a flash tube, a lens 30, a mirror 31, a ring slit 32 having a ring-shaped opening, a lens 33, a light intercepting plate 34 insertable into the optical path 02, an apertured mirror 35 having an opening in the central portion thereof, a front eye part observation lens 36 insertable into the optical path 02, and an objective lens 37. Rearwardly of the apertured mirror 35, there are arranged in succession a longitudinally movable focusing lens 38, an imaging lens 39, a quick return mirror 40 capable of quickly returning to a position outside of the optical path, and film 41.

In the reflection direction of the quick return mirror 40, there are disposed a magnifying lens 42 insertable into the optical path, a TV lens 43 and a TV camera 44, the output of which is connected to a TV monitor 45 and TV signal memory means 46. An imprinting monitor 47 for reproducing a stored image and data is connected to the TV signal memory means 46 so as to imprint the image into the film 41 through the intermediary of a lens 48 and a mirror 49. A switch 46a for reproducing the stored image on the TV monitor 45, like the switch 15a of FIG. 1, is connected to the TV signal memory means 46. Further, a front eye part illuminating infrared light source 50 is provided forwardly of and above the objective lens 37, and a dichroic mirror 51 is made insertable into the optical path, and in the incidence direction thereof, there are disposed a lens 52 and an eye interior illuminating infrared light source 53 so that the front eye part and the interior of the eye can be illuminated. A variable resistor 53a as one of means for changing the luminance of the infrared light source 53 is connected to the infrared light source 53.

Figure 10:
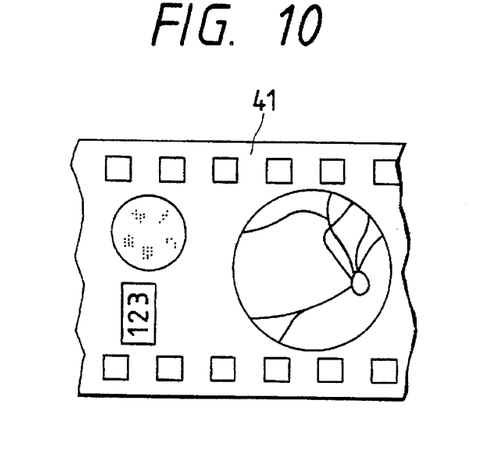
FIG. 10 is an illustration of film.

During alignment, the light intercepting plate 34 is inserted into the optical path to thereby intercept the light from the light source 26. When the front eye part observation lens 36 and the dichroic mirror 51 are inserted into the optical path and the front eye part illuminating infrared light source 50 and the eye interior illuminating infrared light source 53 are turned on, the front eye part and the interior of the eye E to be examined are illuminated. The presence or absence of turbidity of the interior of the eye is ascertained by the TV camera 44, and the TV image is received by the TV signal memory means 46. Subsequently, the light intercepting plate 34, the front eye part observation lens 36 and the dichroic mirror 51 are retracted out of the optical path, and the eye fundus photographing light source 29 is turned on with the quick return mirror 40 being returned to a position outside the optical path. Thereupon, the image of the fundus of the eye is picked up by the film 41 and at the same time, the imprinting monitor 47 is turned on, and the data and the image of the front eye part are also imprinted onto the film 41 as shown in FIG. 10.

During the observation of the front eye part, the magnifying lens 42 may be inserted into the optical path to effect magnified observation. For this magnified observation, the magnifying lens 42 may be used or the signal may be electrically magnified. The projection-imaging state and the reflecting state of light projected from the infrared light source 53 to the fundus of the eye are varied by the refractive power of the eye to be examined and the observed brightness of the light is also varied. Therefore, as means for correcting this, the luminance of the light source 53 may be adjusted by the variable resistor 53a in response to the movement of the focusing lens 38. The correction of the brightness may be effected by the light source 53 or the lens 52 being moved in the direction of the optical axis.

Figure 11:
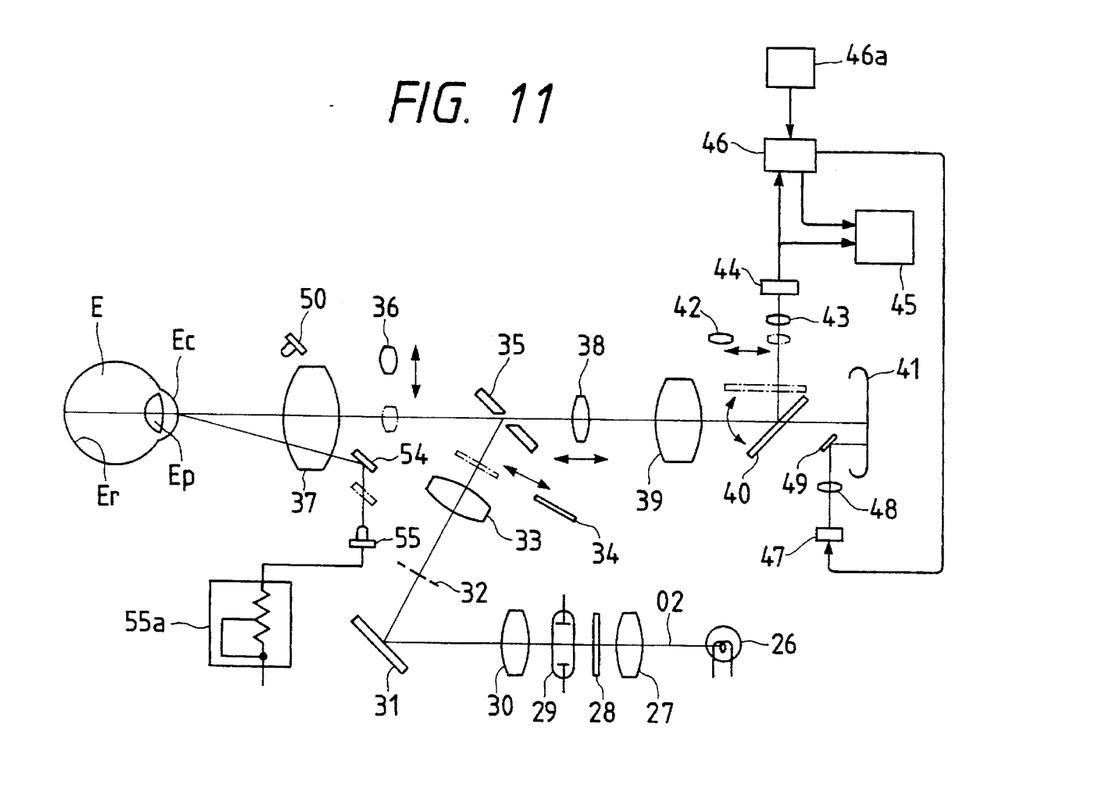
FIG. 11 shows the construction of a fourth embodiment of the present invention.

FIG. 11 shows the construction of a fourth embodiment which is a modification of the third embodiment. A mirror 54 and an eye interior illuminating infrared light source 55 for illuminating the interior of the eye are provided rearwardly of the objective lens 37 so as not to overlap the optical path. Again in this case, a variable resistor is connected to the infrared light source 55.

During the photographing of the front eye part, the front eye part illuminating infrared light source 50 and the eye interior illuminating infrared light source 55 are turned on to illuminate the front eye part and the interior of the eye, respectively. As in the above-described third embodiment, the image of the front eye part and the image of the fundus of the eye are recorded on the film 41. Since the mirror 54 is disposed rearwardly of the objective lens 37, the examinee will not feel discomfort, and since a large distance can be provided between the objective lens 37 and the eye E to be examined, operability is improved.

As described above, in the infrared ray observation ophthalmologic apparatus according to each of the above-described embodiments, it becomes possible to ascertain the presence or absence of turbidity in the light transmitting body of the eye to be examined by illuminating the interior of the eye, and if an abnormality in the measured refraction value or flare in the photographed image of the fundus of the eye is observed, the cause thereof can be determined.

A retinal camera according to each of embodiments which will hereinafter be described is provided with an objective lens opposed to an eye to be examined, a projection optical system for projecting an image of the fundus of the eye to be examined formed by the objective lens onto a predetermined observation and image pickup surface, and front eye part observation means for making the image of the front eye part of the eye to be examined conjugate with the predetermined observation and image pickup surface. The making of the image conjugate with the surface is performed with an optical member removably provided between the objective lens and the image pickup surface. The retinal camera also comprises a light source for illuminating the eye to be examined substantially coaxially with the optical axis of the objective lens by the removable insertion of the optical member, coaxial illuminating means having first polarizing means for polarizing the light from the light source, and observation means for observing the front eye part of the eye to be examined through second polarizing means having a direction of polarization orthogonal to that of the first polarizing means.

The retinal camera hereinafter described also records the fundus of the eye to be examined, and further comprises presenting means for presenting to the examiner the name of a disease and a classified list of various kinds of information which become necessary to read the image of the fundus of the eye, selecting means for selecting the recording of the information presented by the presenting means, and recording means for recording the information selected by the selecting means, together with the image of the fundus of the eye to be examined.

In the retinal camera having the above-described construction, during the observation of the front eye part, the eye to be examined is illuminated by polarized light substantially coaxial with the optical axis of the objective lens, and the observation of only polarized light orthogonal to the front eye part illuminating light is effected.

Also, in this retinal camera, the examiner selects an appropriate information item, whereby the item necessary to read the image of the fundus of the eye can be recorded with the image of the fundus of the eye.

Embodiments shown in FIGS. 12 to 16 will hereinafter be described in detail.

Figure 12:
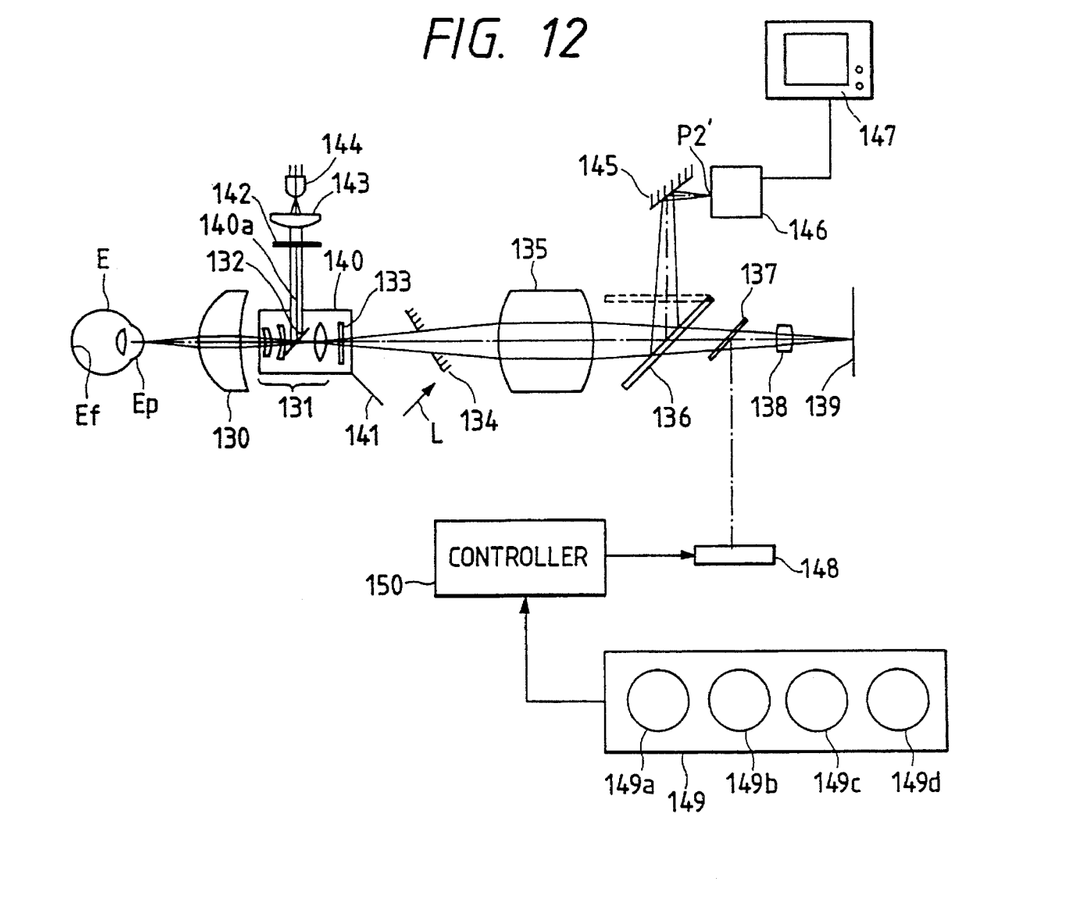
FIG. 12 shows the construction of a fifth embodiment of the present invention.

FIG. 12 shows a retinal camera of the non-mydriasis type. Forwardly of an eye E to be examined, there are arranged along the visual axis an objective lens 130, an auxiliary lens 131 comprising a plurality of lenses, a half mirror 132 provided in the auxiliary lens 131, a polarizing plate 133, an apertured mirror 134, a relay lens 135, a movable mirror 136, a half mirror 137, a lens 138 and film 139. The auxiliary lens 131, the half mirror 132 and the polarizing plate 133 are contained in a lens housing 140 insertable into the optical path, and an opening 140a for effecting the coaxial illumination of the front eye part therethrough is formed in the upper portion of the housing 140, and a light intercepting plate 141 for cutting eye fundus illuminating light L during the observation of the fundus of the eye and during the exposure of the film is provided below the housing 140. Although not shown, an eye fundus illuminating system similar to that disposed below the apertured mirror 35 of FIGS. 9 and 11 (on the optical path 02) is disposed below the aperture mirror 134. The method of photographing the fundus of the eye is similar to what has been previously described.

On the optical path of the eye fundus coaxially illuminating optical system above the opening 140a, there are disposed a polarizing plate 142 having a direction of polarization orthogonal to that of the polarizing plate 133, a condenser lens 143 and a coaxially illuminating light source 144 emitting near infrared light. Also, in the reflection direction of the movable mirror 136, there are provided an optical path deflecting mirror 145 and a TV camera 146 having a sensitivity to near infrared light. The output of the camera 146 is connected to a TV monitor 147. The half mirror 137 and lens 138 are of a small size, and these are provided at locations somewhat eccentric in a direction perpendicular to the plane of the drawing sheet relative to a photographing system, and in the incidence direction thereof, there is disposed a display element 148, to which is connected the output of a switch 149 having four switches 149a, 149b, 149c and 149d through a controller 150.

The state of the apparatus shown in FIG. 12 is the front eye part observing state in which with the housing 140, and the auxiliary lens 131 are inserted in the optical path. Near infrared light emitted from the coaxially illuminating light source 144 has only its linearly polarized component selected through the condenser lens 143 and the polarizing plate 142, whereafter it is directed into the pupil Ep of the eye E to be examined coaxially with the visual axis thereof via the opening 140a in the housing 140, the half mirror 132, the auxiliary lens 131 and the objective lens 130. The thus directed light is scattered and reflected at the center of the fundus Ef of the eye and illuminates the crystalline lens from within the eye. The image of the front eye part of the eye E to be examined is displayed on the TV monitor 147 by the TV camera 146 placed on an observation surface P2' and having sensitivity to near infrared light, and the examiner observes this and effects the alignment of the apparatus, and so-called thorough illumination observation for judging the state of the front eye part is obtained.

Front eye part observation light is directed to the TV camera 146 through the polarizing plate 133 having a direction of polarization in a direction orthogonal to the polarizing plate 142 and thus, the regularly reflected component from the lens portion which the illuminating light beam to the front side portion of the auxiliary lens 131, the objective lens 130 and the cornea of the eye E to be examined, and the observation light beam use in common is blocked and a ghost-free thorough illuminated image of the crystalline lens is displayed on the TV monitor 147.

Figure 13:
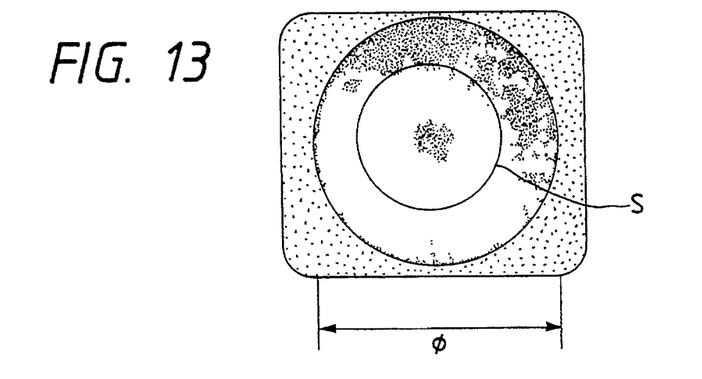
FIG. 13 illustrates the thoroughly illuminated image of the front eye part.

In FIG. 13, which shows that state, the central white image is the crystalline lens and the outside thereof is the pupil Ep. Sporadical dark shadows inside the crystalline lens are formed due to the reflected light from the fundus of the eye being scattered by a cataract and the quantity of the observation light is thereby decreased. By seeing these shadows, the examiner can know the extent of the cataract of the eye E to be examined.

Also, in FIG. 13, a circle S electrically synthesized by means, not shown, indicates the minimum pupil diameter ϕ photographable by the present apparatus, and by comparing the pupil diameter ϕ with the diameter of the circle S, the examiner can ascertain the size of the pupil Ep. By aligning this circle S and the pupil Ep of the eye to be examined substantially similarly, the examiner can also accomplish the alignment of the apparatus at the same time.

After ascertaining these, the examiner retracts the auxiliary lens 131, i.e., the housing 140, from the optical path and performs the operation of photographing the fundus of the eye. In order to make the state of this ascertainment useful during the reading of the photograph of the fundus of the eye, an information imprinting function is provided. The switch 149 is an input switch for effecting the imprinting of this information; specifically, the switch 149a is used when the pupil Ep is small, the switch 149b is used in the case of an eye having a cataract, the switch 149c is used in the case of the examinee having diabetes, and the switch 149d is utilized in the case of the examinee having hyperpiesia.

When the examiner closes the switch 149, the signal thereof is input to the controller 150 for controlling the entire apparatus, and it is displayed on the display element 148. The display by the display element 148 is imaged on a side edge portion of the film 139 through the intermediary of the mirror 137 and lens 138, disposed at locations eccentric from the photographing system, and is recorded on the film 139 together with the image of the fundus of the eye.

Figure 14:
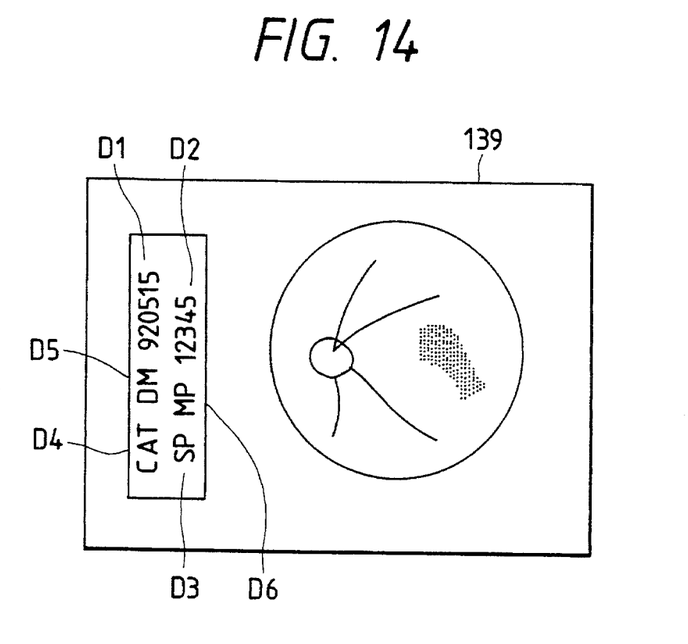
FIG. 14 illustrates film having information imprinted therein.

FIG. 14 shows the film 139 having these bits of information imprinted therein, and the image of the fundus of the eye and a data recording portion are recorded on the film 139. Besides ordinary date data D1 and a patient number D2, the display D3 of an item SP indicating that the pupil Ep is small and corresponding to the input from the input switch 149a, the display D4 of an item CAT indicating the presence of a cataract and corresponding to the input from the switch 149b, the display D5 of an item DM indicating the presence of diabetes, and the display D6 of an item MP indicating the presence of hyperpiesia, are recorded as information on the data recording portion.

Figure 15:
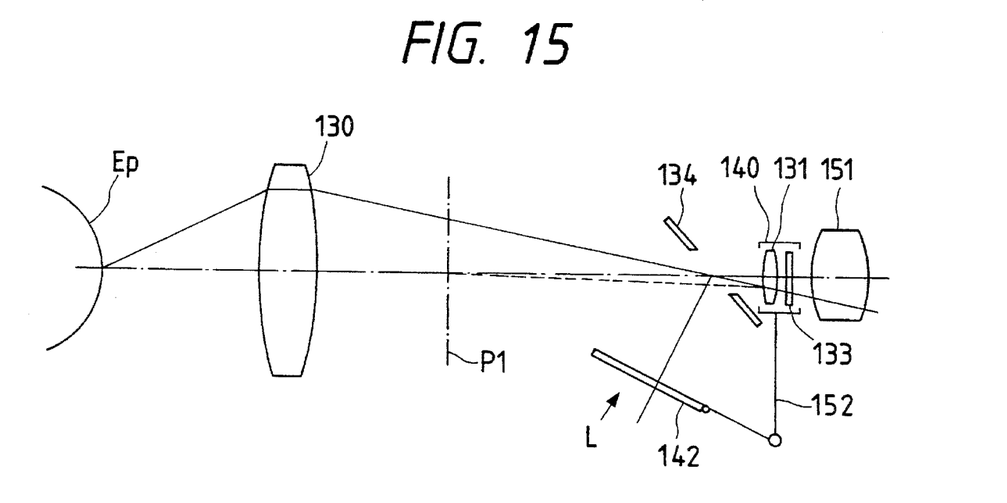
FIG. 15 shows the construction of a sixth embodiment of the present invention.

While a retinal camera having a coaxially illuminating light source discrete from an eye fundus illuminating light source has been shown in the embodiment of FIG. 12, it is also possible to use these light sources in common. FIG. 15 shows the construction of such a sixth embodiment in which the coaxially illuminating light source and the eye fundus illuminating light source are used in common. An auxiliary lens 131 is a convex lens inserted between the eye fundus imaging position P1 by an objective lens 130 and a relay lens 151, and is provided on the relay lens 151 side of an apertured mirror 134. Polarizing plates 133 and 142 are provided in an observation system and an illuminating system, respectively, as shown in FIG. 12, and the polarizing plate 133 and the auxiliary lens 131 are housed in a housing 140. The polarizing plate 142 is coupled to the housing 140 by a link mechanism 152 so that it may be inserted into the optical path of illuminating light L (i.e., the optical path O2) simultaneously with the insertion of the auxiliary lens 131 into the optical path.

Accordingly, the eye fundus illuminating system requires no change during the observation of the front eye part and therefore, the coaxially illuminating light beam and the eye fundus illuminating light beam can be used in common. Placing the auxiliary lens 131 at this location not only leads to the advantage that the illuminating systems can be used in common, but also is effective to permit setting the observation magnification of the front eye part to effect a more detailed thorough illumination observation.

As can be seen from this example, the means for making the front eye part of the eye E to be examined conjugate with the image pickup surface is not limited to that mentioned in this embodiment. For example, two mirrors can be insertably provided in the optical path to ensure an optical path of great length, or means of the type which bypasses the relay lens 151 can be used.

Also, the above embodiment has been described with respect to a retinal camera of the non-mydriasis type, but the present invention is also applicable to a retinal camera of the mydriasis type which enables the fundus of the eye to be directly observed by the naked eye, by using visible light as the coaxially illuminating means.

In the above-described embodiment, there has been discussed an example in which the kinds of information which can be input are limited to four kinds, but it is possible to record information in a memory provided in the controller 150, read out this information and allot it via the input switch 149 to thereby increase the kinds of selected information. To accomplish such allotment via the switch 149 relatively simply, the input switch 149 can be a bezel switch which effects the display of information on a TV monitor screen.

Figure 16:
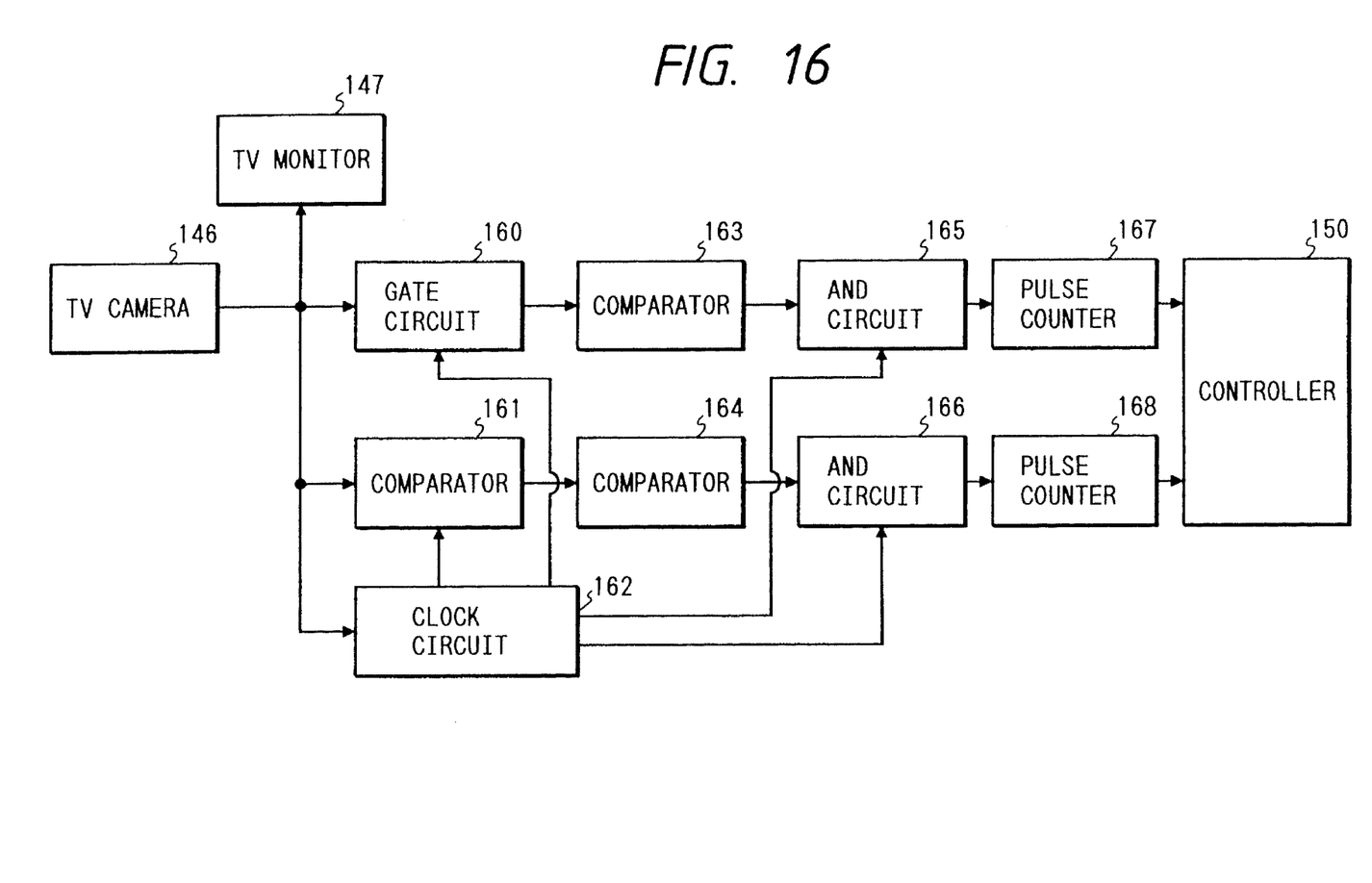
FIG. 16 is a block diagram of an information processing circuit.

Also, the apparatus itself automatically judges and records information such as data representing the existence of small pupils and cataracts, whereby the significance of a group examination will be enhanced. FIG. 16 shows a block diagram of such an information processing circuit. The TV camera 146 is connected to the TV monitor 147, gate circuits 160, 161 and a clock circuit 162, and the gate circuits 160 and 161 are connected to comparators 163 and 164, respectively, the outputs of which are connected to the controller 150 through AND circuits 165, 166 and pulse counters 167, 168, respectively. The output of the clock circuit 162 is connected to the gate circuits 160, 161 and the AND circuits 165, 166.

A video signal with a synchronizing signal output from the TV camera 146 is input into the two gate circuits 160, 161 and the clock circuit 162 parallel to the output to the TV monitor 147. The gate circuits 160 and 161 have the function of counting pulses from the clock circuit 162 on the basis of the input synchronizing signal, and outputting the video signal of a particular area. The gate circuit 160, as shown in FIG. 16, outputs a video signal within the range in the circle S on the TV monitor 147 and outputs a signal representing the degree of severity of a cataract. In contrast, the gate circuit 161 extracts several scanning lines near the central portion of the scanning line on the TV monitor 147 and outputs a signal representing the diameter of the pupil. These signals are binarized in the comparators 160 and 161, respectively, and the product thereof with the reference clock signal from the clock circuit 162 is input to the AND circuit 165. The outputs of pulse counters 167 and 168 are input to the controller 150, which compares the outputs thereof with a reference value and effects a judgment relating to the cataract by the output of the pulse counter 167 and effects a judgment relating to the existence of a small diameter pupil by the output of the pulse counter 168.

The judgment is carried out during an arbitrary time when the front eye part is being observed, and the then proper value is judged by the controller 150, which thus determines the output of the display element 148. The examiner ascertains this judgment at the end of the observation of the front eye part and shifts to the performing of a photographing operation. As regards the reference value of the aforementioned binarizing process, it is desirable to effect an adaptation procedure such as automatically setting the reference value to ½ of the maximum value of the last frame.

As described above, according to the above-described retinal camera, alignment can be easily accomplished by inserting the auxiliary lens, and according to the above-described retinal camera, necessary information can be recorded with the image of the fundus of the eye during the photographing of the image of the fundus of the eye.

What is claimed is:

1. An ophthalmologic apparatus comprising:

an examining system for examining an eye and outputting an examination result;

an illuminating system comprising a light source for illuminating a fundus of the eye through a pupil area of the eye with infrared light;

an image pickup camera comprising an image pickup surface, conjugate with an anterior part of the eye, for receiving infrared light reflected from the fundus of the eye, and thereby picking up an image formed by the infrared light reflected from the fundus of the eye whose state of turbidity corresponds to the state of turbidity of a light transmitting body portion of the eye and producing corresponding output image data; and an output system for receiving the examination result and the output image data, and for producing an output representing the state of turbidity with an output representing the examination result.

2. The ophthalmologic apparatus of claim 1, further comprising a television monitor for displaying the output image data.

3. The ophthalmologic apparatus of claim 2, further comprising a memory portion for storing the output image data and for outputting the stored image data, said television monitor displaying the stored image data output from said memory portion.

4. The ophthalmologic apparatus of claim 1, said output system comprising a recording portion for recording the output representing the state of turbidity, said recording portion being capable of recording the output representing the state of turbidity with the output representing the examination result output.

5. The ophthalmologic apparatus of claim 1, wherein said illuminating system further comprises a lens system for directing illumination from said light source to the fundus of the eye, and a brightness correcting portion for correcting a brightness of said light source, said brightness correcting portion comprising means for effecting at least one of a driving of at least one of a position of said light source and a position of said lens system in a direction of an optical axis and a varying of the luminance of said light source to thereby effect brightness correction.

6. The ophthalmologic apparatus of claim 5, said examining system comprising a retinal camera portion for observing the fundus of the eye, wherein said brightness correcting portion effects the brightness correction in accordance with a focusing operation during an observation of the fundus of the eye with said retinal camera.

7. The ophthalmologic apparatus of claim 1, further comprising a magnifying projection system for effecting a magnified projection of the eye when the image of the fundus of the eye is picked-up by said image pickup camera.

8. The ophthalmologic apparatus of claim 1, said examining system comprising a retinal camera portion for observing the anterior part of the eye and the fundus of the eye using infrared light and for photographing the fundus of the eye using white light, thereby producing an image of the fundus of the eye, said retinal camera portion having an objective lens and a beam splitter, wherein said beam splitter is disposed on a side of said objective lens adjacent to the eye, and wherein said illuminating system projects the infrared light through said beam splitter.

9. The ophthalmologic apparatus of claim 8, further comprising a memory portion for storing the output image data, the stored output image data being capable of being printed on a film with the image of the fundus of the eye photographed by said retinal camera portion.

10. The ophthalmologic apparatus of claim 1, said examining system comprising a refractometer portion for measuring a refractive power of the eye using a refractometer infrared light that is discrete from the infrared light of said illuminating system, said refractometer portion having an objective lens and a beam splitter, wherein said beam splitter is disposed on a side of said objective lens adjacent to the eye, and wherein said illuminating system illuminates the fundus of the eye with infrared light through said beam splitter.

11. The ophthalmologic apparatus of claim 10, wherein said beam splitter is retractable out of an optical path.

12. The ophthalmologic apparatus of claim 1, wherein said output system comprises a recording portion for recording the output representing the state of turbidity, and wherein the examination result is a measurement of said refractometer portion, said recording portion being capable of recording the output representing the state of turbidity with the output representing the examination result.

13. The ophthalmologic apparatus of claim 1, further comprising an optical system for directing the light reflected from the fundus of the eye to said image pickup camera, said illuminating system illuminating the fundus of the eye through an optical member closer to an object in said optical system than said image pickup camera.

14. The ophthalmologic apparatus of claim 13, further comprising a light intercepting member disposed so as to allow only illuminating light from said illuminating system to travel toward said image pickup camera.

15. The ophthalmologic apparatus of claim 1, wherein said illuminating system is operational to provide illumination only during a particular time.

16. The ophthalmologic apparatus of claim 1, wherein said illuminating system illuminates the fundus of the eye from a direction of a visual axis.

17. The ophthalmologic apparatus of claim 1, said examining system comprising a retinal camera portion for recording an image of the fundus of the eye, presenting means for presenting to an operator of said apparatus a list of information necessary to read the image of the fundus of the eye, selecting means for selecting information presented by said presenting means, and recording means for recording the selected information with the image of the fundus of the eye.

18. The ophthalmologic apparatus of claim 17, wherein the selected information includes information regarding the state of turbidity of the light transmitting body portion of the eye observed by said image pickup camera.

19. The ophthalmologic apparatus of claim 17, wherein said selecting means selects the information automatically in accordance with the output image data from said image pickup camera.

20. An ophthalmologic apparatus comprising:

an illuminating system comprising a light source for illuminating a fundus of an eye to be examined through a pupil area of the eye with infrared light;

an objective lens facing the eye;

a projection optical system for projecting an image of the fundus of the eye formed through said objective lens;

an image pickup camera, comprising an image pickup surface conjugate with an anterior part of the eye, said image pickup surface receiving infrared light reflected from the fundus of the eye and projected thereto by said projection optical system;

an output system for outputting data representing a state of turbidity of a light transmitting body portion of the eye in accordance with an image picked-up by said image pickup camera;

an optical member, insertably provided between said objective lens and said image pickup surface, for making an image of the anterior part of the eye conjugate with said image pickup surface, wherein said illuminating system further comprises first polarizing means for polarizing the light from said light source and illuminating the eye through said optical member when said optical member is in an inserted state, and wherein said image pickup camera receives light through second polarizing means having a direction of polarization orthogonal to that of said first polarizing means.

21. The ophthalmologic apparatus of claim 20, wherein said light source illuminates the fundus of the eye during the image pickup of the fundus of the eye.

22. A retinal camera usable with an insertable optical member, said retinal camera comprising:

an objective lens facing an eye to be examined;

a projection optical system for projecting an image of a fundus of the eye formed through said objective lens onto a predetermined image pickup surface;

optical means for making an image of an anterior part of the eye conjugate with the predetermined image pickup surface when the optical member is inserted between said objective lens and the predetermined image pickup surface;

a light source for illuminating the eye when the optical member is inserted between said objective lens and the predetermined image pickup surface;

first polarizing means for polarizing the light from said light source, the eye being illuminated with the light from said light source through said first polarizing means;

second polarizing means having a direction of polarization orthogonal to that of said first polarizing means; and observation means for enabling observation of the anterior part of the eye through an image formed on the predetermined image pickup surface from light reflected from the eye and through said second polarizing means.

23. The retinal camera of claim 22, wherein said light source emits near infrared light, and wherein said observation means uses the near infrared light to enable observation of the anterior part of the eye.

24. The retinal camera of claim 22, wherein said light source is also used for illuminating the fundus of the eye.

25. A retinal camera comprising:

a camera portion for photographing a fundus of an eye, thereby producing an image of the fundus of the eye;

presenting means for presenting to an operator of said camera a list of information usable to examine an image of the fundus of the eye photographed by said camera portion;

switch means for selecting information from the list presented by said presenting means; and recording means for recording the selected information with the image of the fundus of the eye photographed by said camera portion.

26. A retinal camera comprising:

a camera portion for photographing a fundus of an eye, thereby producing an image of the fundus of the eye;

presenting means for presenting to an operator of said camera a list of information usable to examine an image of the fundus of the eye photographed by said camera portion;

switch means for selecting information from the list presented by said presenting means;

recording means for recording the selected information with the image of the fundus of the eye photographed by said camera portion; and anterior eye part observation means for observing an anterior part of the eye, wherein the information selected by said switch means represents an image of the anterior part of the eye including at least one of an image of an eye showing mydriasis of the eye and an image showing a turbidity of a light transmitting portion of the eye.

27. The retinal camera of claim 26, wherein said anterior eye part observation means includes photoelectric image pickup means, and wherein said switch means automatically selects information in accordance with an output of said photoelectric image pickup means.

* * * * *

UNITED STATES PATENT AND TRADEMARK OFFICE
CERTIFICATE OF CORRECTION

PATENT NO.   :   5,455,644
DATED        :   October 3, 1995
INVENTOR(S)  :   KOJI YAZAWA, ET AL.

It is certified that error appears in the above-indentified patent and that said Letters Patent is hereby corrected as shown below:

COLUMN 2

Line 47, change "On" to --On--.

COLUMN 9

Line 64, change "result output." to --result.--.

COLUMN 10

Line 17, change "picked-up" to --picked up--.
　　　Line 45, change "Claim 1" to --Claim 10--.

COLUMN 11

Line 32, change "picked-up" to --picked up--.

Signed and Sealed this

Seventh Day of May, 1996

Attest:

BRUCE LEHMAN

*Attesting Officer*　　　Commissioner of Patents and Trademarks